(12) United States Patent
Mascarenhas

(10) Patent No.: US 7,288,516 B1
(45) Date of Patent: Oct. 30, 2007

(54) NULL IGF FOR THE TREATMENT OF CANCER

(75) Inventor: Desmond Mascarenhas, San Jose, CA (US)

(73) Assignee: Celtrix Pharmaceuticals, Inc., Richmond, VA (US)

( * ) Notice: Subject to any disclaimer, the term of this patent is extended or adjusted under 35 U.S.C. 154(b) by 443 days.

(21) Appl. No.: 09/399,120

(22) Filed: Sep. 20, 1999

(51) Int. Cl.
*A61K 38/30* (2006.01)

(52) U.S. Cl. .............................. 514/2; 514/3; 530/303

(58) Field of Classification Search ................. 514/12; 530/303, 324, 399
See application file for complete search history.

(56) References Cited

U.S. PATENT DOCUMENTS

| | | | |
|---|---|---|---|
| 5,187,151 A | 2/1993 | Clark et al. | 514/12 |
| 5,310,742 A | 5/1994 | Elias | 514/274 |
| 5,407,913 A | 4/1995 | Sommer et al. | 514/12 |
| 5,473,054 A * | 12/1995 | Jameson et al. | 530/328 |
| 5,527,776 A | 6/1996 | Carlino et al. | 514/12 |
| 5,643,867 A | 7/1997 | Maack et al. | 530/350 |
| 5,681,818 A | 10/1997 | Spencer et al. | 514/12 |
| 5,723,441 A | 3/1998 | Higley et al. | 514/12 |

FOREIGN PATENT DOCUMENTS

| | | |
|---|---|---|
| WO | WO 95/03817 | 2/1995 |
| WO | WO 95/04076 | 2/1995 |
| WO | WO 95/13823 | 5/1995 |
| WO | 95/16703 | 6/1995 |
| WO | WO 96/02565 | 2/1996 |
| WO | WO 96/40722 | 12/1996 |
| WO | WO 97/39032 | 10/1997 |
| WO | 98/36764 | 8/1998 |

OTHER PUBLICATIONS

Bayne et al. 'The Role of Tyrosines 24, 31, and 60 in the High Affinity Binding of Insulin-Like Growth Factor-I to the Type 1 Insulin-Like Growth Factor Receptor', Journal of Biological Chemistry, vol. 265, No. 26, Sep. 15, pp. 15648-15652.*

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491-495. 1994.*

Rudinger, J. (1976). Peptide Hormones (ed. J.A. Parsons). University Park Press. Baltimore. pp. 1-7.*

Berendsen, Herman, "A Glimpse of the Holy Grail?", Science, vol. 282, pp. 642-643, Oct. 23, 1998.*

"Computerized Drug Design: Still Promising, Not Yet Here", Science, vol. 256, pp. 441, Apr. 24, 1992.*

Jain, Rakesh, Delivery of Molecular Medicine to Solid Tumors, Science, vol. 271, p. 1079-1080, Feb. 1996.*

Dermer, Gerald. Anotehr Anniversary for the War on Cancer, Bio/Technolgoy, vol. 12, Mar. 1994.*

Gura, Trisha. Systems for Identifying New Drugs are Often Faulty, Science, vol. 278, pp. 1041-1042. Nov. 1997.*

Golden, Fredrick, Of Mice and Men: Don't Blame the Rodents, Time, pp. 44, May 18, 1998.*

Adams et al., 1996, "Pharmacokinetics and bioavailability of rhIGF-I/IGFBP-3 in the rat and monkey" *Prog. Growth Factor Res.* 6(2-4):347-356.

Ausubel et al., 1987, *Current Protocols in Molecular Biology*, John Wiley & Sons, Inc., New York, (Table of Contents).

Baxter et al., 1986, "Growth hormone-dependent insulin-like growth factor (IGF) binding protein from human plasma differs from other human IGF binding proteins" *Biochem. Biophys. Res. Comm.* 139(3):1256-1261.

Baxter et al., 1989, High molecular weight insulin-like growth factor binding protein complex *J. Biol. Chem.* 264(20):11843-11848.

Baxter et al., 1992, "Structural determinants for binary and ternary complex formation between insulin-like growth factor-I (IGF-I) and IGF binding protein-3" *J. Biol. Chem.* 267:60-65.

Baxter, Robert C., 1988, "Characterization of the acid-labile subunit of the growth hormone-dependent insulin-like growth factor binding protein complex" *J. Clin. Endocrinol. Metab.* 67:265-272.

Bayne et al., 1990, "The roles of tyrosines 24,31, and 60 in the high affinity binding of insulin-like growth factor-I to the type 1 insulin-like growth factor receptor" *J. Biol. Chem.* 265:15648-15652.

Blum et al., 1991, "Plasma IGFBP-3 levels as clinical indicators" *Modern Concepts in Insulin-like Growth Factors*, E.M. Spencer, ed., Elsevier, New York, pp. 381-393.

Butler et al., 1998, "Stimulation of tumor growth by recombinant human insulin-like growth factor-I (IGF-I is dependent on the dose and the level of IGF-I receptor expression" *Cancer Res.* 58:3021-3027.

(Continued)

*Primary Examiner*—Anish Gupta
(74) *Attorney, Agent, or Firm*—Beth A. Burrous; Foley & Lardner LLP

(57) ABSTRACT

New methods for the treatment of cancer are provided. Null IGF (IGF variants with reduced receptor binding) is administered to subjects having cancer, thereby alleviating the symptoms of the cancer.

39 Claims, 2 Drawing Sheets

OTHER PUBLICATIONS

Cascieri et al., 1988, "Mutant of human insulin-like growth factor I with reduced affinity for the type 1 insulin-like growth factor receptor" *Biochemistry* 27:3229-3233.

Cascieri et al., 1989, "Structural analogs of human insulin-like growth factor (IGF) I with altered affinity for type 2 IGF receptors" *J. Biol. Chem.* 264(4):2199-2202.

Favoni et al., 1998, "Modulation of the insulin-like growth factor-I system by N-(4-hydroxyphenyl)-retinamide in human breast cancer cell lines" *Br. J. Cancer* 77(12): 2138-2147.

Giuliano et al., 1998, "Induction of apoptosis in human retinoblastoma cells by topoisomerase inhibitors" *Invest Ophthalmol. Vis. Sci.* 39(8): 1300-1311.

Karas et al., 1997, "Membrane-associated insulin-like growth factor-binding protein-3 inhibit insulin-like growth factor-I-induced insulin-like growth factor-I receptor signaling in Ishikawa endometrial cancer cells" *J. Biol. Chem.* 272(26):16514-16520.

Kelley et al., 1998, "Insulin growth factor-I inhibits apoptosis in hematopoietic progenitor cells" *Ann. N. Y. Acad. Sci.* 840: 518-524.

Leal et al., 1997, "The type V transforming growth factor β receptor is the putative insulin-like growth factor-binding protein 3 receptor" *J. Biol. Chem.* 272(33):20572-20576.

Lee et al., 1995, "Purified rat acid-labile subunit and recombinant human insulin-like growth factor (IGF)-binding protein-3 can form a 150-kilodalton binary complex in vitro in the absence of IGFs" *Endocrinology* 136(11):4982-4989.

Nickerson et al., 1997, "Insulin-like growth factor binding protein-3 induces apoptosis in MCF7 breast cancer cells". *Biochem. Biophys. Res. Comm.* 237:690-693.

Rajah et al., 1997, "Insulin-like growth factor (IGF)-binding protein-3 induces apoptosis and mediates the effects of transforming growth factor-β1 on programmed cell death through a p53- and IGF-independent mechanism" *J. Biol. Chem.* 272(18):12181-12188.

Rinderknecht et al., 1976, "Polypeptides with nonsuppressible insulin-like and cell-growth promoting activities in human serum: Isolation, chemical characterization, and some biological properties of forms I and II" *Proc. Natl. Acad. Sci. USA* 73(7):2365-2369.

Sambrook et al., 1989, *Molecular Cloning: A Laboratory Manual*, vols. 1-3 Cold Spring Harbor Laboratory Press, 2nd ed., (Table of Contents).

Sommer et al., 1991, "Molecular genetics and actions of recombinant insulin-like growth factor binding protein-3", *Modern Concepts of Insulin-like Growth Factors*, E.M. Spencer, ed., Elsevier, New York, pp. 715-728.

Toms et al., 1998, "Antagonist effect of insulin-like growth factor I on protein kinase inhibitor-mediated apoptosis in human glioblastoma cells in association with bcl-2 and bcl-$X_L$" *J. Neurosurg.* 88: 884-889.

Xu et al., 1997, "Multiple myeloma cells are protected against dexamethasone-induced apoptosis by insulin-like growth factors" *Br. J. Haematol.* 97: 429-440.

Yang et al., 1996, "Heparin inhibition of insulin-like growth factor-binding protein-3 binding to human fibroblats and rat glioma cells: Role of heparan sulfate proteoglycans" *Endocrinology* 137(10):4363-4371.

Zadeh et al., 1997, "The 16-kDA proteolytic fragment of insulin-like growth factor (IGF) binding protein-3 inhibits the mitogenic action of fibroblast growth factor on mouse fibroblasts with a targeted disruption of the type 1 IGF receptor gene" *Endocrinology* 138(7):3069-3072.

Zawada et al., 1998, "Growth factors improve immediate survival of embryonic dopamine neurons after transplantation into rats" *Brain Res.* 786: 96-103.

* cited by examiner

FIG. 1

1                                                              50
GPETLCGAEL VDALQFVCGD RGFYFNKPTG YGSSSRRAPQ TGIVDECCFR 51                 70
SCDLRRLEMY CAPLKPAKSA

NULL IGF FOR THE TREATMENT OF CANCER

TECHNICAL FIELD

The invention relates to the field of treatment of cancer, and particularly to the use of null IGF for the treatment of cancer.

BACKGROUND ART

Growth factors are polypeptides which stimulate a wide variety of biological responses (e.g. DNA synthesis, cell division, expression of specific genes, etc.) in a defined population of target cells. A variety of growth factors have been identified, including the transforming growth factor beta family (TGF-βs), epidermal growth factor and transforming growth factor alpha (the TGF-αs), the platelet-derived growth factors (PDGFs), the fibroblast growth factor family (FGFs) and the insulin-like growth factor family (IGFs), which includes IGF-I and IGF-II. Many growth factors have been implicated in the pathogenesis of cancer.

IGF-I and IGF-II (the "IGFs")are related in amino acid sequence and structure, with each polypeptide having a molecular weight of approximately 7.5 kilodaltons (kDa). IGF-I mediates the major effects of growth hormone, and is thus the primary mediator of growth after birth. IGF-I has also been implicated in the actions of various other growth factors, since the treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division).

IGF-I has been found to stimulate the growth of cells from a number of different types of cancer (Butler et al., 1998 *Cancer Res.* 58(14):3021-3027; Favoni R E, et al., 1998, *Br. J. Cancer* 77(12): 2138-2147). Additionally, IGF-I has additionally been found to exert anti-apoptotic effects on a number of different cell types, including tumor cells (Giuliano M, et al., 1998 *Invest Ophthalmol. Vis. Sci.* 39(8): 1300-1311; Zawada W M, et al., 1998, *Brain Res.* 786(1-2): 96-103; Kelley K W, et al., 1998, *Ann. N.Y. Acad. Sci.* 840: 518-524; Toms S A, et al., 1998, *J. Neurosurg.* 88(5): 884-889; Xu F, et al., 1997, *Br. J. Haematol.* 97(2): 429-440). U.S. Pat. No. 5,681,818 claims the administration of IGFBP-3 for the treatment of cancer.

A number of variant forms of IGF-I have been created which have altered binding characteristics for the IGF receptors, the insulin receptor, or IGFBP's (Cascieri et al. (1988) Biochemistry 27:3229-3233 and (1989) Jr. Biol. Chem. 264:2199-2202; Bayne et al. (1990) J. Biol. Chem. 265:15648-15652; Baxter et al. (1992) J. Biol. Chem. 267:60-65). Additionally, International Patent Application No. WO 97/39032 discloses the use of certain variant forms of IGF-I for the treatment of conditions where increased IGF-I activity is desired, such as diabetes, osteoporosis, and the like. The variant forms of IGF-I are proposed to displace IGF-I from IGFBP, resulting in increased IGF-I activity.

Almost all IGF circulates in a non-covalently associated complex of IGF-I, insulin-like growth factor binding protein 3 (IGFBP-3) and a larger protein subunit termed the acid labile subunit (ALS), such that very little free IGF-I is detectable. The ternary complex is composed of equimolar amounts of each of the three components. ALS has no direct IGF-binding activity and appears to bind only to the IGF/IGFBP-3 complex (Baxter et al., *J. Biol. Chem.* 264(20): 11843-11848, 1989), although some reports suggest that IGFBP-3 can bind to rat ALS in the absence of IGF (Lee et al., *Endocrinology* 136:4982-4989, 1995). The ternary complex of IGF/IGFBP-3/ALS has a molecular weight of approximately 150 kDa and has a substantially increased half-life in circulation when compared to binary IGF/IGFBP-3 complex or IGF alone (Adams et al., *Prog. Growth Factor Res.* 6(24):347-356; presented October 1995, published 1996). This ternary complex is thought to act "as a reservoir and a buffer for IGF-I and IGF-II preventing rapid changes in the concentration of free IGF" (Blum et al (1991), "Plasma IGFBP-3 Levels as Clinical Indicators" in MODERN CONCEPTS OF INSULIN-LIKE GROWTH FACTORS, pp. 381-393, E. M. Spencer, ed., Elsevier, N.Y.). While there is essentially no excess (unbound) IGFBP-3 in circulation, a substantial excess of free ALS does exist (Baxter, *J. Clin. Endocrinol. Metab.* 67:265-272, 1988).

It should be noted that, while IGFBP-3 is the most abundant of the IGF binding proteins ("IGFBPs"), at least five other distinct IGFBPs have been identified in various tissues and body fluids. Although these proteins bind IGFs, they originate from separate genes and have distinct amino acid sequences. Unlike IGFBP-3, other circulating IGFBPs are not saturated with IGFs. IGFBP-3 and IGFBP-5 are the only known IGFBPs which can form the 150 kDa ternary complex with IGF and ALS. The IGF and ALS binding domains of IGFBP-3 are thought to be in the N-terminal portion of the protein, as N-terminal fragments of the protein isolated from serum retain these binding activities. However, some of the other IGFBPs have also been suggested for use in combination with IGF-I as therapeutics.

In addition to its role as the major carrier protein for IGF in serum, IGFBP-3 has been recently shown to have a number of different activities. IGFBP-3 can bind to an as-yet unidentified molecule on the cell surface, where it can inhibit the activity of exogenously-added IGF-I (Karas et al., 1997, *J. Biol. Chem.* 272(26):16514-16520). Although the binding of IGFBP-3 to cell surfaces can be inhibited by heparin, the unidentified cell surface binding molecule is unlikely to be a heparin-like cell surface glycosaminoglycan, because enzymatic removal of heparin glycosaminoglycans has no effect on IGFBP-3 cell surface binding (Yang et al., 1996, *Endocrinology* 137(10):4363-4371). It is not clear if the cell surface binding molecule is the same as or different than the IGFBP-3 receptor that was identified by Leal et al. (1997, *J. Biol. Chem.* 272(33):20572-20576), which is identical to the type V transforming growth factor-beta (TGF-β) receptor.

IGFBP-3 has also been found to promote apoptosis. Interestingly, IGFBP-3 has been shown to promote apoptosis in cells with and without functional type 1 IGF receptors (Nickerson et al., 1997, *Biochem. Biophys. Res. Comm.* 237(3):690-693; Rajah et al., 1997, *J. Biol. Chem.* 272(18): 12181-12188). However, there are conflicting reports as to whether apoptosis is induced by full length IGFBP-3 or a proteolytic fragment of IGFBP-3 (Rajah et al., ibid; Zadeh et al., 1997, *Endocrinology* 138(7):3069-3072).

IGF-I and IGFBP-3 may be purified from natural sources or produced by recombinant means. For instance, purification of IGF-I from human serum is well known in the art (Rinderknecht et al. (1976) *Proc. Natl. Acad. Sci. USA* 73:2365-2369). Production of IGF-I by recombinant processes is shown in EP 0 128 733, published in December of 1984. IGFBP-3 may be purified from natural sources using a process such as that shown in Baxter et al. (1986, *Biochem. Biophys. Res. Comm.* 139:1256-1261). Alternatively, IGFBP-3 may be synthesized by recombinantly as discussed in Sommer et al., pp. 715-728, MODERN CONCEPTS OF INSULIN- LIKE GROWTH FACTORS (E. M. Spencer, ed., Elsevier, N.Y., 1991). Recombinant IGFBP-3 binds IGF-I in a 1:1 molar ratio.

Topical administration of IGF-I/IGFBP-3 complex to rat and pig wounds is significantly more effective than administration of IGF-I alone (Id.). Subcutaneous administration of IGF-I/IGFBP-3 complex to hypophysectomized, ovariectomized, and normal rats, as well as intravenous administration to cynomolgus monkeys, "substantially prevents the hypoglycemic effects" of IGF-I administered alone (Id.).

The use of IGF/IGFBP-3 complex has been suggested for the treatment of a wide variety of disorders (see, for example, U.S. Pat. Nos. 5,187,151, 5,527,776, 5,407,913, 5,643,867, 5,681,818 and 5,723,441, as well as International Patent Applications Nos. WO 95/03817, WO 95/13823, and WO 96/02565. IGF-I/IGOFBP-3 complex is also under development by Celtrix Pharmaceuticals, Inc., as a treatment for several indications, including recovery from burns and recovery from hip fracture surgery.

While there are a large number of cytotoxic drugs available for the treatment cancer, these drugs are generally associated with a variety of serious side effects, including alopecia, leukopenia, mucositis. Accordingly, there is a need in the art for cancer therapies that do not induce the serious side effects associated with conventional cytotoxic chemotherapy.

DISCLOSURE OF THE INVENTION

The inventor has surprisingly found that null IGF-I, administered in the absence of IGFBP-3, is effective in alleviating the symptoms of cancer, whereas null IGF-I administered as a complex with IGFBP-3 is ineffective. This finding was unexpected because IGFBP-3 is known to substantially increase the half-life of IGF-I and to increase the efficacy of IGF-I (Sommer et al., supra), so it was expected that null IGF-I/IGFBP-3 complex would be more efficacious in alleviating the symptoms of cancer than null IGF-I administered in the absence of IGFBP-3.

Disclosed herein are methods for alleviating the symptoms of cancer. In one embodiment, an effective amount of null IGF is administered to a subject having cancer, thereby alleviating the symptoms of the cancer.

In another embodiment, a thyroid axis antagonist is administered with the null IGF-I to the subject having cancer.

DEFINITIONS

As used herein, the term "null IGF-I" refers to IGF-I which has amino acid sequence alterations at one or more sites in the molecule. Null IGF-I retains its ability to bind IGFBP-3, but is altered in its receptor binding and/or activating properties (e.g., having little or no binding to the type 1 IGF receptor while maintaining its binding activities for the type 2 IGF receptor and the insulin receptor). A preferred null IGF-I has substantially reduced binding to both types of the IGF receptor and the insulin receptor. Descriptions of null IGF-I's may be found in Cascieri et al. (1988) *Biochemistry* 27:3229-3233; (1989) *J. Biol. Chem.* 264:2199-2202), Bayne et al. (1990) *J. Biol. Chem.* 265:15648-15652) and Baxter et al. (1992) *J. Biol. Chem.* 267:60-65). Examples of null IGF-I include variants in which one or more of IGF-I's tyrosine residues (i.e., residues 24, 31, or 60) are replaced with non-aromatic residues (i.e., other than tyrosine, phenylalanine or tryptophan), variants where amino acid residues 49, 50, 51, 53, 55 and 56 are altered (for example, where residues 49-50 are altered to Thr-Ser-Ile or where residues 55-56 are altered to Tyr-Gln), and combinations thereof.

The term "thyroid axis antagonist" refers to a compound which acts to decrease thyroid hormone activity in a subject. Thyroid axis antagonists include 6-n-propyl-2-thiouracil (propylthiouracil or PTU), methimazole, carbimazole, and other compounds known to the art to reduce thyrotropic hormones, thyroid hormones, or thyroid receptor signaling.

BRIEF DESCRIPTION OF THE DRAWINGS

FIG. 1 shows the amino acid sequence (SEQ ID NO: 1) of native human IGF-I in single-letter amino acid code.

BEST MODE FOR CARRYING OUT THE INVENTION

Figure 2:
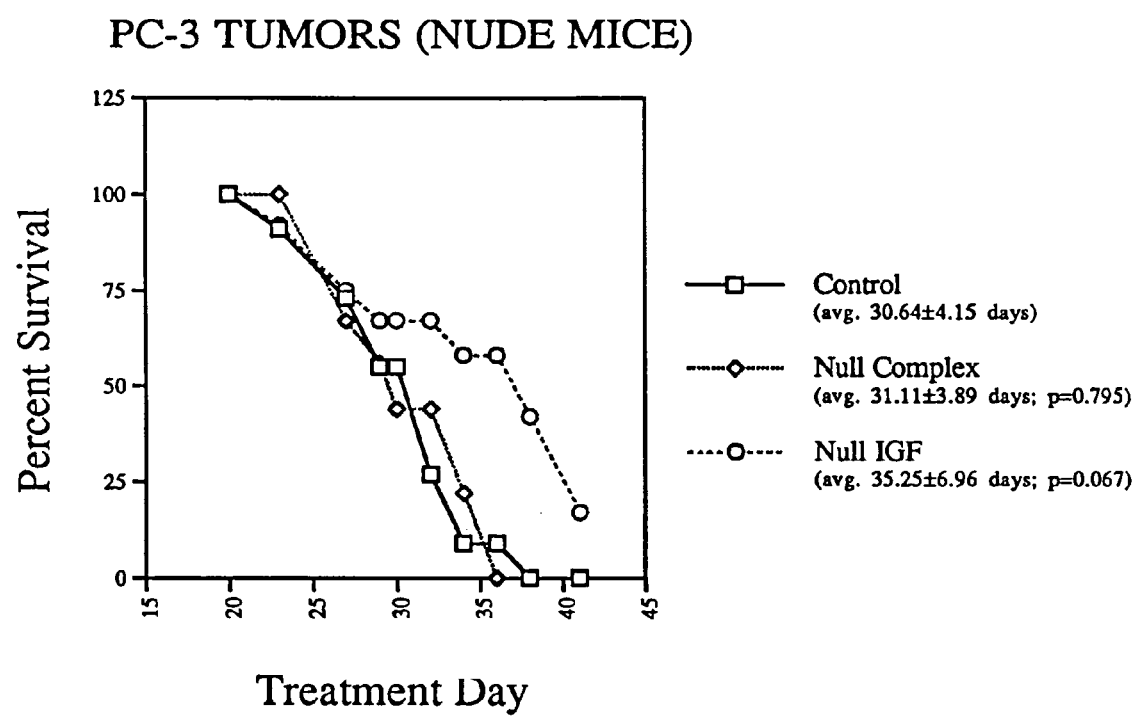
FIG. 2 depicts the results of the experiment described in Example 2. The percentage of surviving animals (y-axis) is plotted against time after xenograft implantation (x-axis). The data for $null_{60}$ IGF-I, $null_{60}$ complex and control treated groups are represented by open circles, open diamonds and open squares, respectively.

Disclosed herein are new methods for the treatment of cancer. An effective amount of null IGF-I is administered to a subject suffering from cancer, thereby alleviating the symptoms of the cancer. Null IGF-I slows the growth rate of cancer, thereby alleviating the symptoms of, or slowing the progression of the cancer. While not wishing to be bound by any particular theory, the inventor believes that the administration of null IGF-I displaces native IGF-I from complexes with binding proteins, particularly binding proteins other than IGFBP-3 (e.g., IGFBP-2), resulting in reduced IGF-I activity, which reduces growth of the tumor and renders the tumor cells more responsive to apoptotic signals.

The inventors have surprisingly found that administration of null IGF-I is substantially more effective at slowing tumor growth than the administration of null IGF-I as a complex with IGFBP-3. This was surprising because it is well known that uncomplexed IGF-I has a significantly shorter half-life than IGF-I administered as a complex with IGFBP-3 and that IGF-I administered as a complex with IGFBP-3 is more effective than uncomplexed IGF-I.

Null IGF-I may be used to treat any cancer, preferably carcinomas such as breast, prostate, cancer and lung cancers.

Null IGF-I for use in accordance with the instant inventive methods may be derived from any species, although species-matched null IGF-I (i.e., null IGF-I based on the native sequence from the same species as the subject to which the IGF-I is to be administered) is preferred. Null IGF-I for use in the instant invention is uncomplexed null IGF-I, that is, administered in the absence of IGFBP-3 (i.e., is not administered as null IGF-I/IGFBP-3 complex), and is preferably administered in the absence of any IGF binding protein.

The null IGF-I is normally produced by recombinant methods, which allow the production of all possible variants in IGF-I sequence. Techniques for the manipulation of recombinant DNA are well known in the art, as are techniques for recombinant production of proteins (see, for example, in Sambrook et al., MOLECULAR CLONING: A LABORATORY MANUAL, Vols. 1-3 (Cold Spring Harbor Laboratory Press, 2 ed., (1989); or F. Ausubel et al., CURRENT PROTOCOLS IN MOLECULAR BIOLOGY (Green Publishing and Wiley-Interscience: New York, 1987) and periodic updates).

Preferably, the null IGF-I is produced using a bacterial cell strain as the recombinant host cell. An expression construct (i.e., a DNA sequence comprising a sequence encoding the desired null IGF-I operably linked to the necessary DNA sequences for proper expression in the host cell, such as a promoter and/or enhancer elements at the 5' end of the construct and terminator elements in the 3' end of the construct) is introduced into the host cell. The DNA sequence encoding the null IGF may optionally linked to a sequence coding another protein (a "fusion partner"), to form a fusion protein. Preferably, the DNA sequence encoding the null IGF-I is linked to a sequence encoding a fusion partner as described in International Patent Application No. WO 94/04076. The expression construct may be an extra-chromosomal construct, such as a plasmid or cosmid, or it may be integrated into the chromosome of the host cell, for example as described in International Patent Application No. WO 96/40722.

Null IGF-I is preferably administered by parenteral administration, including but not limited to intravenous (IV), intraperitoneal (IP), intramuscular (IM), subcutaneous (SC), intradermal (ID), transdermal, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The null IGF-I may also be delivered in a slow release formulation adapted for IV, IP, IM, ID or SC administration. Inhaled null IGF-I is preferably delivered in discrete doses (e.g., via a metered dose inhaler adapted for protein delivery). Administration of null IGF-I via the transdermal route may be continuous or pulsatile.

For parenteral administration, compositions of null IGF-I may be in dry powder, semi-solid or liquid formulations. For parenteral administration by routes other than inhalation, the null IGF-I is preferably administered in a liquid formulation. Null IGF-I formulations may contain additional components such as salts, buffers, bulking agents, osmolytes, antioxidants, detergents, surfactants, and other pharmaceutical excipients as are known in the art.

Null IGF-I is administered to subjects having cancer at a dose of about 0.01 to about 50 mg/kg/day, more preferably about 0.1 to about 20 mg/kg/day, more preferably 0.5 to about 15 mg/kg/day, even more preferably about 1 to about 10 mg/kg/day.

In certain embodiments, the null IGF-I is administered to the subject with a thyroid axis antagonist. The administration of the two compounds may be simultaneous, overlapping, or separated in time, as long as the subject experiences exposure to both compounds at the same time. Where the two compounds are formulated for the same route and schedule of administration, the administration is preferably simultaneous or nearly simultaneous (e.g., concurrent or serial injections). However, in some embodiments, the routes and schedules of administration for the two compounds will be different, making simultaneous administration inconvenient. A subject will be considered to have been administered null IGF-I and a thyroid axis antagonist if the subject experiences simultaneous systemic exposure to both compounds, regardless of when or how the compounds were administered.

In methods requiring the administration of thyroid axis antagonists with the null IGF-I, the dose of the thyroid axis antagonist is normally titrated for the individual subject, as is well known in the art. Induction of frank hypothyroidism is not required, though in some cases it may be found advantageous, for the proper working of this invention. Thyroid axis antagonists are generally administered at an intermediate dose, and the patient observed for the onset of hypothyroidism. Hypothyroidism may be recognized by its well known symptoms, including (in adults) lethargy, constipation, cold intolerance, menorrhagia (in women of reproductive age), reduced intellectual and motor activity, dry hair, dry skin, muscle aches, reduced auditory acuity, and deepening and hoarsening of the voice. In extreme cases, florid myxedema may be present, as indicated by a dull, expressionless face, sparse hair, periorbital puffiness, enlarged tongue and pale, cool skin which feels rough and doughy. The thyroid antagonist dose should be reduced if florid myxedema appears, to avoid the possibility of myxedema coma, a serious and frequently fatal condition. Upon the appearance of the signs of hypothyroidism which fall short of florid myxedema, the dose of the thyroid axis antagonist may be reduced to the point at which the symptoms of hypothyroidism resolve, as will be understood by one of skill in the art.

Thyroid axis antagonists may be produced in any formulation known to the art, including parenteral and oral dosage forms. Oral formulations are preferred, but parenteral formulations are also acceptable, and may be more convenient in an in-patient setting. Formulations for parenteral administration are generally formulated as liquids, but may also be in gel or solid depot form. Formulations for oral administration are generally in tablet or capsule form, although syrups and liquids are also acceptable. Formulations of thyroid axis antagonists generally include excipients, such as salts, buffers, bulking agents, detergents, binding agents, surfactants, stabilizers, preservatives, anti-oxidants, lubricants, coating agents, and other pharmaceutically acceptable excipients as are known in the art.

The dosage of thyroid axis antagonist should be adjusted according to the identity, formulation and route of administration of the thyroid axis antagonist which is administered with the null IGF-I, as is known in the art. Where the thyroid axis antagonist is propylthiouracil, the dose of propylthiouracil may be from 1 to 400 mg/day. A subject is normally initiated with a dose of 50 to 400 mg/day, typically divided into three equal doses, and maintained at 50 to 100 mg/day divided into two or three equal doses. For methimazole and carbimazole, the dose may be from 0.1 to 50 mg/day. Typically, a subject is initiated with 5 to 50 mg/day, and maintained on 1 to 5 mg/day.

The patents, patent applications, and publications cited throughout the disclosure are incorporated herein by reference in their entirety.

EXAMPLES

Example 1

Pharmacokinetics of Null IGF-I

The pharmacokinetics of three test articles were assayed: (1) a recombinant human null IGF-I (Y60L IGF-I), in which the normal tyrosine residue at position 60 had been substituted with leucine; variant recombinant human IGFBP-3 (N109D,N172D IGFBP-3), in which the asparagine residues normally at positions 109 and 172 were substituted with aspartate; and Y60L IGF-I/N109D,N172D IGFBP-3 complex at a 1:1 molar ratio. Nine mice, each weighing approximately 20-25 grams were utilized in the study. Mouse were housed in standard mouse cages, one per cage, and fed with water and mouse chow ad libitum.

Y60L IGF-I, N109D,N172D IGFBP-3, and Y60L IGF-I/N109D,N172D IGFBP-3 complex were dissolved in 50 mM sodium acetate, pH 5.5, 108 mM NaCl, at 2, 8, and 10 mg/ml, respectively. The animals were randomly divided into three groups of three animals each.

The animals received 100 µl of the undiluted appropriate test article in a single subcutaneous bolus. Blood samples (approximately 50 µl each) were collected by eye-bleeds at 0.08, 1, 2, 4, and 8 house after the injection. Serum was isolated from each sample, and assayed for human IGF-I and IGFBP-3, as appropriate, using commercially-available immunoassay kits obtained from DSL (Webster, Tex.) according to the manufacturer's instructions. The approximate area under the curve (AUC) was calculated by multiplying concentrations by the time periods between samples for each animal, and mean AUC's (in arbitrary units) were determined for each group. The results are shown in Table I ("nd" indicates that the assay was not performed).

TABLE I

| Test Article | Dose (mg/kg) | $AUC_{IGF-I}$ | $AUC_{IGFBP-3}$ |
|---|---|---|---|
| Y60L IGF-I | 10 | 2,597 | nd |
| N109D/N172D IGFBP-3 | 40 | nd | 15,480 |
| Y60L IGF-I/N109D, N172D IGFBP-3 complex | 50 | 7,505 | 37,797 |

The data clearly indicates that, as expected, administration of null IGF-I as a complex with IGFBP-3 substantially increases systemic exposure to null IGF-I, as indicated by the substantial increase in AUG.

Example 2

Treatment of Prostate Cancer Tumors with Null IGF41

Y60L IGF-I and Y60L IGF-I/N109D,N172D IGFBP-3 complex were tested for anti-tumor activity in nude mice. 36 mice which had been implanted with PC-3 (human prostate) tumor xenografts were obtained from the Goodwin Cancer Institute (Plantation, Fla.). Each mouse had received a subcutaneous xenograft of approximately 4-6 mm$^3$ solid PC-3 tumor.

Three different test articles were employed in this experiment: 2 mg/kg/day Y60L IGF-I ("null$_{60}$ IGF-I") dissolved in 50 mM sodium acetate, pH 5.5, 108 mM sodium chloride ("vehicle"); 10 mg/kg/day Y60L IGF-II/N109D,N172D IGFBP-3 complex ("null$_{60}$ IGF-I complex") dissolved in vehicle; and vehicle alone ("control"). The test articles were administered near the xenograft site twice each weekday (Monday through Friday) and once per weekend day (Saturday and Sunday) by subcutaneous bolus injection. Test articles were administered from day 15 after implantation ("Day 15") until the animal was sacrificed.

Animals were sacrificed at day 57 after implantation ("Day 57") or earlier if tumor volume exceeded 2000 mm3. Tumor growth was measured three times per week using calipers. Statistical analysis was performed using a two-tailed t test.

Any animal that did not show evidence of tumor growth by Day 23 was eliminated from the study. 12 null$_{60}$ IGF-1,9 null$_6$O IGF-I complex, and 11 control treated mice remained in the study after Day 23.

Results of this experiment are depicted graphically in FIG. 2. Survival of the control and null$_{60}$ complex animals were very similar (average survival 30.6 days and 31.1 days, respectively, p=0.795). However, mice treated with nu160 IGF-I had substantially greater survival, with an average survival of 35.25 days at the end of the study (p=0.067 compared with control). It should be noted that the average survival of the null$_{60}$ IGF-I treated mice was underestimated by this experiment, as two null$_{60}$ IGF-I treated mice had tumors of less than 2000 mm3 at the end of the study. Inspection of FIG. 2 also reveals that median survival was substantially increased for mice receiving null$_{60}$ IGF-I.

The present invention has been detailed both by direct description and by example. Equivalents and modifications of the present invention will be apparent to those skilled in the art, and are encompassed within the scope of the invention.

The invention claimed is:

1. A method for slowing the growth rate of a tumor, comprising: administering an effective amount of uncomplexed null insulin-like growth factor I (IGF-I) to a subject having cancer.

2. The method of claim 1, wherein said cancer is selected from the group consisting of breast, prostate, colon and lung cancer.

3. The method of claim 2, wherein said cancer is breast cancer.

4. The method of claim 2, wherein said cancer is prostate cancer.

5. The method of claim 2, wherein said cancer is colon cancer.

6. The method of claim 2, wherein said cancer is lung cancer.

7. The method of claim 1, wherein the residue at position 60 of the amino acid sequence of said null IGF-I is altered to a non-aromatic residue.

8. The method of claim 7, wherein the residue at position 24 or 31 of said amino acid sequence of said null IGF-I is additionally altered to a non-aromatic residue.

9. The method of claim 7, wherein said null IGF-I is additionally altered at a position selected from the group of positions 49, 50, 51, 53, 55 and 56.

10. The method of claim 1, wherein said null IGF-I is administered at about 0.01 to about 50 milligrams per kilogram total body weight per day (mg/kg/day).

11. A method for slowing progression of a cancer comprising:
administering an effective amount of uncomplexed null insulin-like growth factor I (IGF-I) to a subject having cancer, thereby slowing progression of the cancer.

12. The method of claim 1, wherein the residue at position 60 of the amino acid sequence of said null IGF-I is altered to a leucine residue.

13. The method of claim 1, wherein the residue at position 24 of the amino acid sequence of said null IGF-I is a non-aromatic residue.

14. The method of claim 13, wherein the residue at position 31 of said amino acid sequence of said null IGF-I is a non-aromatic residue.

15. The method of claim 1, wherein the residues at positions of 24, 31 and 60 of the amino acid sequence of said null IGF-I are altered to a non-aromatic residue.

16. The method of claim 7, wherein said cancer is breast cancer.

17. The method of claim 7, wherein said cancer is prostate cancer.

18. The method of claim 7, wherein said cancer is colon cancer.

19. The method of claim 7, wherein said cancer is lung cancer.

20. The method of claim 8, wherein said cancer is breast cancer.

21. The method of claim 8, wherein said cancer is prostate cancer.

22. The method of claim 8, wherein said cancer is colon cancer.

23. The method of claim 8, wherein said cancer is lung cancer.

24. The method of claim 13, wherein said cancer is breast cancer.

25. The method of claim 13, wherein said cancer is prostate cancer.

26. The method of claim 13, wherein said cancer is colon cancer.

27. The method of claim 13, wherein said cancer is lung cancer.

28. The method of claim 14, wherein said cancer is breast cancer.

29. The method of claim 14, wherein said cancer is prostate cancer.

30. The method of claim 14, wherein said cancer is colon cancer.

31. The method of claim 14, wherein said cancer is lung cancer.

32. The method of claim 15, wherein said cancer is breast cancer.

33. The method of claim 15, wherein said cancer is prostate cancer.

34. The method of claim 15, wherein said cancer is colon cancer.

35. The method of claim 15, wherein said cancer is lung cancer.

36. The method of claim 12, wherein said cancer is prostate cancer.

37. The method of claim 11, wherein the residue at position 60 of the amino acid sequence of said null IGF-I is altered to a non-aromatic residue.

38. The method of claim 37, wherein said non-aromatic residue is a leucine residue.

39. The method of claim 37 or 38, wherein said cancer is prostate cancer.

* * * * *

SEQUENCE LISTING

```
<160> NUMBER OF SEQ ID NOS: 1

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
 65                  70
```